United States Patent
Crotty et al.

[11] Patent Number: 5,993,838
[45] Date of Patent: Nov. 30, 1999

[54] COSMETIC PRODUCT FOR REMOVAL OF KERATOTIC PLUGS FROM SKIN PORES

[75] Inventors: Brian Andrew Crotty, Branford; Philip Edward Miner, Newtown; Johnson Anthony, Fairfield; Alexander Paul Znaiden, Trumbull; Jaime Varela, Hamden, all of Conn.

[73] Assignee: Chesebrough-Pond's USA Co.,, Greenwich, Conn.

[21] Appl. No.: 09/012,707

[22] Filed: Jan. 23, 1998

Related U.S. Application Data

[60] Provisional application No. 60/039,378, Mar. 20, 1997, and provisional application No. 60/070,876, Jan. 9, 1998.

[51] Int. Cl.$^6$ .......................... A61K 9/70; A61K 31/765; A61K 31/79
[52] U.S. Cl. .................. 424/402; 424/78.02; 514/846
[58] Field of Search ................................. 424/401, 402; 206/363, 570, 581; 514/846

[56] References Cited

U.S. PATENT DOCUMENTS

| | | | |
|---|---|---|---|
| 3,086,647 | 4/1963 | Krezanoski | 206/363 |
| 4,126,142 | 11/1978 | Saute . | |
| 4,752,472 | 6/1988 | Kligman . | |
| 4,762,124 | 8/1988 | Kerch et al. . | |
| 4,990,339 | 2/1991 | Scholl et al. . | |
| 5,026,552 | 6/1991 | Gueret et al. . | |
| 5,254,338 | 10/1993 | Sakai et al. . | |
| 5,302,446 | 4/1994 | Horn | 424/402 |
| 5,466,456 | 11/1995 | Glover . | |
| 5,512,277 | 4/1996 | Uemura et al. . | |
| 5,658,582 | 8/1997 | Dorigatti et al. | 424/402 |
| 5,723,138 | 3/1998 | Bae et al. . | |
| 5,736,128 | 4/1998 | Chaudhuri et al. . | |
| 5,753,246 | 5/1998 | Peters | 206/581 |
| 5,811,107 | 9/1998 | Gangadharan et al. | 424/401 |

FOREIGN PATENT DOCUMENTS

| | | |
|---|---|---|
| 206114 | 11/1959 | Austria . |
| 0 063 875 | 4/1982 | European Pat. Off. . |
| 0 309 309 | 3/1989 | European Pat. Off. . |
| 0 514 760 | 11/1992 | European Pat. Off. . |
| 2538247 | of 0000 | France . |
| 2 734 574 | 5/1995 | France . |
| 55-127312 | of 0000 | Japan . |
| 63-35511 | of 0000 | Japan . |
| 63-57508 | of 0000 | Japan . |
| 9-194325 | of 0000 | Japan . |
| 56119499 | 7/1981 | Japan . |
| 56120577 | 7/1981 | Japan . |
| 2 144 133 | 2/1985 | United Kingdom . |
| 87/05206 | 9/1987 | WIPO . |
| 98/05283 | 2/1988 | WIPO . |
| 93/05893 | 4/1993 | WIPO . |
| 96/14822 | 5/1996 | WIPO . |
| 97/32567 | 9/1997 | WIPO . |

OTHER PUBLICATIONS

"Les masques de beaute" by A. Julien et al., *Parfums, Cosmetiques, aromes*, No. Dec. 1986 Translation of KAO Biore Package (Japan)—1997.
International Search Report.
"Proposing New Lifestyles. Superiior Product Creation: Biore Pore Back"—available from Internet: *URL://HTTP-:WWW.KAO.CO.JP/AR97/PE.HTM,* 1997, XP002072734.

*Primary Examiner*—Peter F. Kulkosky
*Attorney, Agent, or Firm*—Milton L. Honig

[57] ABSTRACT

A cosmetic product is provided for removing keratotic skin plugs. The product is a strip sealed for storage having 2 to 12% moisture within a pouch. The strip includes a flexible substrate sheet onto which a composition containing an adhesive polymer is deposited. The composition is treated to become dry non-tacky to the touch yet upon being wetted for use the composition again turns tacky and mobile. The method of application involves either directly moistening the product or indirectly moistening by first wetting a consumer's face in an area where the product is applied. Thereafter, water is allowed to evaporate leaving a film to which the keratotic plugs are bonded. The film is then peeled away concommittingly removing the plugs.

13 Claims, 1 Drawing Sheet

COSMETIC PRODUCT FOR REMOVAL OF KERATOTIC PLUGS FROM SKIN PORES

This Application claims Benefit of Provisional Application 60/039,378 filed Mar. 20, 1997, also Provisional Application 60/070,876, Jan. 09, 1998.

BACKGROUND OF THE INVENTION

1. Field of the Invention

The invention concerns a cosmetic product effective for the removal of keratotic plugs from skin pores.

2. The Related Art

Highly visual pores on facial skin surfaces are perceived, especially by women, to be a serious beauty problem. The conspicuous nature of this problem is caused by keratotic plugs formed within pores of the skin. Keratotic plugs are dead epidermal cells keratinized together with sebaceous matter and dirt. Absent proper treatment, not only will beauty suffer but also various dermatological problems may arise. Removal with detergents or with make-up removers (e.g. cold cream) have not provided adequate solution to the problem. Squeezing the skin in an attempt to remove keratotic plugs can lead to infections which can damage skin.

Peelable masks have been employed to attack plugged facial pores. They are applied as mobile films to the skin and peeled off after drying. Typically, the film is a nonionic polymer such as polyvinyl alcohol or polyvinyl pyrrolidone. Unfortunately, the mask approach is still not sufficiently effective for removing dirt from skin pores and especially for removing keratotic plugs.

Thus, there remains a need for a remover product which can effectively excise keratotic plugs formed in the pores of the skin and a method of removing keratotic plugs from the skin utilizing such remover products.

U.S. Pat. No. 5,512,277 (Uemura et al.) has reported a keratotic plug remover composition including use of a peelable mask formed from a resin functionalized with salt forming groups. Particularly preferred are cationic polymers which may be delivered as a poultice.

U.S. Pat. No. 4,126,142 (Saute) describes the use of sodium polystyrene sulfonate applied as a film to the face for cleansing skin and diminishing wrinkles. While apparently effective, further improvements in this technology are still necessary.

Accordingly, it is an object of the present invention to provide novel remover products which effectively remove keratotic plugs from skin pores.

It is another object to the present invention to provide new methods for effectively removing keratotic plugs from skin pores.

These and other objects will become more apparent from the summary and detailed description which follow.

SUMMARY OF THE INVENTION

A cosmetic product for removing keratotic plugs from skin pores is provided which includes:

(A) a strip comprising:
 (i) a flexible substrate sheet; and
 (ii) a composition containing a polymer selected from the group consisting of anionic, cationic, nonionic, amphoteric, zwitterionic and polymer mixtures thereof deposited onto the substrate sheet, the composition being dry non-tacky to the touch after deposition and upon being wetted for use the composition turns tacky and mobile; and (B) a pouch sealably enclosing the strip, a volatile fluid also being enclosed present in an amount from 2 to 12% by weight of the strip.

BRIEF DESCRIPTION OF THE DRAWING

The invention will more fully be described by reference to FIG. 1 which is the sole drawing and illustrates a cross section of the cosmetic product.

DETAILED DESCRIPTION

Figure 1:
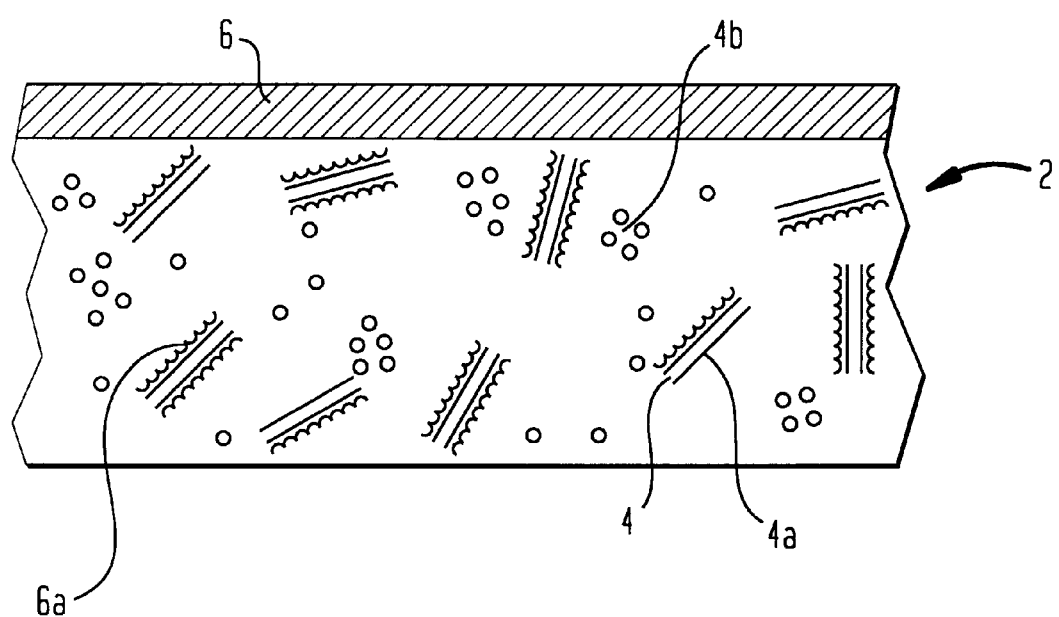

Now it has been discovered that keratotic plugs can be removed by applying to facial skin a cosmetic product in the form of a flexible substrate sheet impregnated with an adhesive composition containing an anionic, cationic, nonionic, amphoteric or zwitterionic polymer. In a dry state, the composition is non-tacky to the touch. The impregnated substrate sheet is sealably enclosed in a pouch, particularly a laminated foil package to maintain a volatile fluid content on the strip or at least within the confines of the sealed pouch in a range from 2 to 12%, preferably from 3 to 10%, optimally from 4 to 8% by weight of the strip. Volataile fluid content within this range is critical. Too much fluid (e.g. moisture) within the pouch causes the strip to stick to walls of the pouch. An aesthetically displeasing sticky substance would thus be delivered to a consumer. Relatively high levels of fluid in the form of moisture are also undesirable because they create mold and mildew. Within the controlled moisture range, the present product is self-preserving. Under relatively low fluid levels, the strip becomes highly brittle and will crack. Most preferred as the volatile fluid is water. However, other liquids can be employed such as $C_1$–$C_4$ alcohols, cyclomethicones, hydrocarbons, ethers and esters. Mixtures of these fluids (e.g. water and alcohol) may also be effectively employed. The volatile fluid should have a boiling point below 200° C., preferably below 120° C.

Pouches of the present invention are normally of the laminated foil variety. These are heat sealed and utilize foils with very low vapor (e.g. moisture) transmission rates (a rate of transmission less than 5% per day, preferably less than 1% per day volatile fluid loss). Walls suitable for the pouch may utilize polyester, polyethylene or polypropylene sheets, several layers of which can be laminated together. These layers may also be provided with a coating of wax or other volatile fluid impermeable material.

The product is used by removing the strip from its pouch and either directly wetting the composition on the sheet or indirectly by wetting the face in areas to be contacted by the composition. In either instance, the wetting agent interacts with the composition so it becomes tacky and sufficiently mobile to flow into skin pores. Pure water is the preferred wetting agent. However, other liquid systems or gels could be employed. Suitable wetting agents would include alcohols such as ethanol, propanol, propylene glycol, polyethylene glycol, polypropylene glycol and especially mixtures of these alcohols with water. Gels would normally consist of structured liquids (particularly water) thickened with structuring agents such as Carbomer.

Subsequent to wetting, the composition is allowed to dry over the area of treatment. During drying the keratotic plugs stickingly adhere to the composition. Advantageously the drying period ranges from 1 minute to 5 hours, preferably from 5 minutes to 1 hour, optimally from 10 to 20 minutes. Thereafter, the dried composition with adhered plugs is peeled from the skin.

Mobility of the composition may be measured by yield point. The yield point should range from 1 to 400 Pascals, preferably from 20 to 200, optimally from 50 to 100 Pascals.

The composition will include an adhesive polymer which may either be anionic, cationic, nonionic, amphoteric, zwitterionic or mixtures thereof. Mixtures may be of polymers within any one category or between different category types. Illustrative of the latter, and a preferred embodiment, is a combination of an anionic and nonionic polymer.

Examples of nonionic polymers suitable for adhesive film deposition are the copolymers of vinyl acetate and crotonic acid, terpolymers of vinyl acetate, crotonic acid and a vinyl ester of an alpha-branched saturated aliphatic monocarboxylic acid such as vinyl neodecanoate; copolymers of methyl vinyl ether and maleic anhydride (molar ratio about 1.1) wherein such copolymers are 50% esterified with a saturated alcohol containing from 1 to 4 carbon atoms such as ethanol or butanol; and acrylic copolymers, terpolymers, etc., containing acrylic acid or methacrylic acid esters of acrylic or methacrylic acid with one or more saturated alcohols having from 1 to 22 carbon atoms such as methyl methacrylate, ethyl acrylate, ethyl methacrylate, n-butyl acrylate, t-butyl acrylate, t-butyl methacrylate, n-butyl methacrylate, n-hexyl acrylate, n-octyl acrylate, lauryl methacrylate and behenyl acrylate, glycols having from 1 to 6 carbon atoms such as hydroxypropyl methacrylate and hydroxyethyl acrylate, styrene, vinyl caprolactam, vinyl acetate, acrylamide, alkyl acrylamides and methacrylamides having 1 to 8 carbon atoms in the alkyl group such as methacrylamide, t-butyl acrylamide and n-octyl acrylamide, and other compatible unsaturated monomers. One specific example is the emulsion polymerized terpolymer of methacrylic acid, n-butyl acrylate and ethyl acrylate (e.g., in a weight percent ratio of 31:42:27, respectively).

Further examples of nonionic adhesive polymers are homopolymers of N-vinylpyrrolidone and copolymers of N-vinylpyrrolidone with compatible nonionic monomers such as vinyl acetate and terpolymers of ethyl acrylate, butyl methacrylate and methyl methacrylate. Nonionic polymers containing N-vinylpyrrolidone in various weight average molecular weights are available commercially from ISP Corporation such as homopolymers of N-vinylpyrrolidone having an average molecular weight of about 630,000 under the trademark PVP K-90 and those having an average molecular weight of about 1,000,000 sold under the trademark of PVP K-120. Particularly preferred is poly(methyl vinyl ether/maleic anhydride) as an unneutralized resin available from ISP Corporation under the trademark Gantrez® S-97 BF.

Anionic adhesive polymers often are derived from the nonionic types which include carboxylic acid functions. Alkaline agents are employed to neutralize the carboxylic acid or anhydride transforming them into anionic salts. Examples of suitable neutralizing agents include 2-amino-2-methyl-1,3-propanediol (AMPD); 2-amino-2-ethyl-1,3-propanediol (AEPD); 2-amino-2-methyl-1-propanol (AMP); 2-amino-1-butanol (AB); monoethanolamine (MEA); diethanolamine (DEA); triethanolamine (TEA); monoisopropanolamine (MIPA); diisopropanol-amine (DIPA); triisopropanolamine (TIPA); and dimethyl stearamine (DMS). Most preferred is AMP.

Particularly preferred anionic polymers are the salts of poly(methyl vinyl ether/maleic anhydride) and polystyrene sulfonic acid. The former is obtained by at least partial neutralization of Gantrez® S-97 BF and the latter available from the National Starch & Chemical Company under the trademarks Versa TL-501 and Flexan® 130 having respective molecular weights of about 500,000 and 100,000. Other polymer films which may be employed and are commercially available as listed in the Table below.

TABLE I

| POLYMER TRADEMARKS (SUPPLIER) | CTFA DESIGNATIONS |
|---|---|
| Resyn ® 28-1310 (NSC) | Vinyl acetate/crotonic acid copolymer |
| Resyn ® 28-2930 (NSC) | Vinyl acetate/crotonic acid/vinyl neodecanoate copolymer |
| Resyn ® 28-2913 (NSC) | Vinyl acetate/crotonic acid/vinyl neodecanoate copolymer |
| Versatyl ® 40 (NSC) | Octylacrylamide/acrylates copolymer |
| Versatyl ® 42 (NSC) | Octylacrylamide/acrylates copolymer |
| Experimental Resin (NSC) | Vinyl acetate/vinyl neodecanoate/maleic half-ester |
| Ultrahold-8 ® (BASF) | Acrylate/acrylamide copolymer |
| Luviset ® CAP (BASF) | Vinyl acetate/crotonic acid/vinyl propionate copolymer |
| PVP K-30 (ISP) | PVP |
| PVP/VA E-335 (ISP) | PVP/Vinyl acetate copolymer |
| PVP/VA E-735 (ISP) | PVP/Vinyl acetate copolymer |
| Gantrez ® ES-225 (ISP) | Ethyl ester of PVM/MA copolymer |
| Gantrez ® ES-425 (ISP) | Butyl ester of PVM/MA copolymer |
| Gaffix ® VC-713 (ISP) | Vinyl caprolactam/PVP/dimethyl aminoethyl methacrylate copolymer |

Cationic adhesive polymers suitable for the present invention may be prepared as homo- or copolymers from monomers including:

Dimethyl aminoethyl acrylate (DMAEA), Dimethylaminoethyl methacrylate (DMAEMA), Dimethylaminopropylacrylamide (DMAPAAm), and Dimethylaminopropyl methacrylamide (DMAPMAAm) which are all (meth)acrylamides or (meth)acrylic acid esters having a dialkylamino group;

Dimethylaminostyrene (DMASt) and Dimethyaminomethylstyrene (DMAMSt) and the like which are styrenes having a dialkylamino group;

4-Vinyl pyridine and 2-vinyl pyridine which are vinyl pyridines; and

Quaternized products of these with a known quaternizing agent such as alkyl halide, benzyl halide, alkyl or aryl sulfonic acid, or dialkyl sulfate.

Among suitable amphoteric adhesive polymers are those derived from monomers such as:

N-(3-sulfopropyl)-N-acryloyloxyethyl-N,N-dimethylammonium betaine, N-(3-sulfopropyl)-N-methacroylamidepropyl-N,N-dimethylammonium betaine, N-(3-carboxymethyl)-N-methacroylamidepropyl-N,N-dimethylammonium betaine and N-carboxymethyl-N-methacroyloxyethyl-N,N-dimethylammonium betaine.

When the salt forming group of the cationic and amphoteric polymers is not ionized, it is preferred to ionize it via neutralization with known acids such as hydrochloric acid and sulfuric acid which are inorganic acids; acetic acid, propionic acid, lactic acid, succinic acid, glycol acid which are organic acids, or with known bases such as triethylamine, trimethylamine which are tertiary amines; ammonia; or sodium hydroxide.

Most polymers suitable for the present invention will be relatively brittle when dried. Therefore, they require a supporting surface which is a flexible substrate sheet. Substrate sheets of the present invention may either be occlusive or non-occlusive. Preferably the sheets are non-occlusive to allow water evaporation from the deposited polymer as the film maturates. Non-occlusivity or breathability is achieved either through use of a hydrophobic substrate having physical porosity (e.g. pore channels) or a hydrophilic substrate wherein the material of construction inherently allows for breathability. Suitable materials include cellulosics such as rayon, wool, cotton, linen, thermoplastic fibers and combinations thereof. They may be woven or nonwoven. Nonwoven rayon is a preferred substrate. Materials formed from combinations of cellulosic with thermoplastic fibers may also be employed. For instance, a hydrophilic polypropylene/rayon combination can be employed for the present invention.

It is advantageous to employ a ratio of composition to substrate in amount ranging from 0.1:1 to 1,000:1, preferably 0.5:1 to 100:1 and optimally 0.8:1 to 10:1 by weight. The polymer ordinarily will constitute from 50 to 100%, preferably from 75 to 99%, optimally from 85 to 95% by weight of the composition deposited onto the substrate sheet.

FIG. 1 provides a cross section of a tape typical of the present invention. The tape is formed of a flexible nonwoven rayon substrate sheet 2. Random fibers 4 are shown laying longitudinally 4a or cut 4b by the cross section. On one surface of the substrate sheet is deposited a composition formed essentially of a polymer 6 which at least partially impregnates the surface. Impregnated polymer 6a is seen as a coating on internal fibers. When wetted, composition 6 turns tacky and can flow into skin pores to adhesively contact keratotic plugs.

Certain additives may be included along with the deposited polymer. Most useful may be a surfactant which can be selected from anionic, cationic, nonionic or amphoteric actives. Illustrative nonionic surfactants are alkoxylated compounds based on $C_{10}$–$C_{22}$ fatty alcohols and acids, and sorbitan. These materials are available, for instance, from the Shell Chemical Company under the Neodol trademark. Copolymers of polyoxypropylene-polyoxyethylene, sold by the BASF Corporation under the Pluronic trademark, are sometimes also useful. Alkyl polyglycosides available from the Henkel Corporation or alkyl glucamides may also be utilized for purposes of this invention.

Anionic type surfactants include fatty acid soaps, sodium lauryl sulphate, sodium lauryl ether sulphate, alkyl benzene sulphonate, mono- and di-alkyl acid phosphates and sodium fatty acyl isethionate.

Amphoteric surfactants include such materials as dialkylamine oxide and various types of betaines (such as cocoamidopropyl betaine).

The surfactant when present may range from 0.01 to 10% by weight of the total composition deposited onto the sheet.

Minor adjunct ingredients may also be included such as fragrances, skin care additives, opacifiers and colorants, each in their effective amounts to accomplish their respective functions.

The following examples will more fully illustrate the embodiments of this invention. All parts, percentages and proportions referred to herein and in the appended claims are by weight unless otherwise indicated.

EXAMPLE 1

A non-woven resin bonded 100% rayon white non-apertured fabric from Vertec was employed as a flexible substrate. Flexan® 130 (sodium salt of sulfonated polystyrene as a 30% polymer in aqueous solution) was deposited onto the rayon fabric.

The fabric for each test strip was a small disk accurately weighed. These disks were submerged in the polymer adhesive solution for about 5 seconds. Thereafter they were dried. Higher loadings were obtained by repeated multiple submergence. To achieve lower loading levels, the 30% aqueous solution was diluted downward to a level of 15% solids and 7.5% solids. These diluted solutions were then used for receiving fabric which was submerged therein.

An area of a panelist's face was chosen which contained several plugged pores. These plugged pores were then counted. Water was applied to the area and the adhesive patch was placed over it. Next, the patch was allowed to dry and then it was peeled off. The number of removed plugs were counted on the adhesive patch. The percent plugs removed was calculated to reflect adhesive patch efficiency. From these values maximum and minimum loading levels were determined.

Calculations:

TABLE I

RESULTS

| % Dried Flexan 130 Loaded on Rayon | % Plugs Pulled |
|---|---|
| 120 | 0 |
| 164 | 90–100 |
| 485 | 90–100 |
| 1100 | 80 |
| 2132 | 70 |
| 3369 | 10 |
| 3815 | 10 |
| 6451 | 10 |

$$\% \text{ Loading} = \frac{(\text{Wt. of rayon with adhesive} - \text{Wt. of dry rayon})}{(\text{Wt. of dry rayon})} \times 100$$

$$\% \text{ Plugs Pulled} = \frac{\text{\# of plugs pulled}}{\text{\# of plugged pores}} \times 100$$

The experiments reported in Table I reveal that there is an optimum loading range for a given adhesive polymer or formulation on a given fabric. It is to be noted that different polymers with different drying rates and even different fabrics may strongly influence plug removal levels.

EXAMPLE 2

A variety of polymers were evaluated for their adhesive effects in removing keratotic plugs from the skin. The polymers listed in Table II below were coated onto a non-woven resin bonded rayon (1 ounce/square yard). A knife-over-roll was utilized in the coating operation. After coating, the non-woven polymer impregnated substrate sheets were dried at 75° C. in a convection oven. They were then cut into small patches.

Similar to the test procedure described under Example 1, the test patches were applied to the face of panelists in an area containing several plugged pores. The plugged pores were counted. Water was applied to the patch and it was then placed over the test area with wet side down. Next, the patch was allowed to dry whereupon it was peeled off. The number of plugs removed were counted as they appeared on the adhesive patch. Percentage of plugs removed were calculated to reflect efficiency of the test product.

TABLE II

| POLYMER | % DRIED POLYMER ON NON-WOVEN | % PLUGS REMOVED |
|---|---|---|
| Dextrine | 409 | 5–15 |
| Polyvinyl Alcohol | 441 | 10–20 |
| Polyvinyl Acetate | 347 | 30–40 |
| Polyacrylamidomethylpropane Sulfonic Acid | 119 | 5–15 |

TABLE II-continued

| POLYMER | % DRIED POLYMER ON NON-WOVEN | % PLUGS REMOVED |
|---|---|---|
| Polyacrylamidomethylpropane Sulfonic Acid | 275 | 25 |
| Poly(methyl vinyl ether/maleic anhydride) | 113 | 90–100 |
| 98% Poly(methyl vinyl ether/maleic anhydride) + 2% 2-amino-2-methyl-1-propanol | 116 | 80–95 |
| 90% Poly(methyl vinyl ether/maleic anhydride) 10% Polyacrylamido methylpropane Sulfonic Acid | 145 | 90–100 |

EXAMPLE 3

Poly(Methyl Vinyl Ether Maleic Anhydride) Gantrez S-97 BF was coated by knife-over-roll (25 mil.) over various nonwoven materials. After coating, the nonwoven materials were dried at 75° C. in a convection oven and then cut into small patches. The test procedure was similar to that reported under Example 2. Results are reported in Table III.

TABLE III

| NONWOVEN | % PLUGS PULLED | OBSERVATIONS |
|---|---|---|
| PGI 5255 Rayon Resin bonded (1 oz./sq. yard) | 90–100 | Nice appearance |
| Veratec 9408810 Polyester/cellulose Wet laid (1.2 oz/sq. yard) | 70–100 | Nice appearance: Nonwoven may be too weak |
| Veratec 2006094 Polypropylene Thermal Bond (.6 oz/sq. yard) | 40–60 | Nice appearance |
| Veratec Polyethylene (.5 oz/sq. yard) | 10 | Poor appearance: When used in application adhesive dried very slow. |

EXAMPLE 4

Strips according to those prepared under Example 3 were packaged in a laminated foil water-impermeable package. The strips were dried prior to sealing within the package to achieve levels reported in the Table below.

TABLE IV

| SAMPLE | PERCENT LOSS ON DRYING | COMMENT |
|---|---|---|
| 1 | 6.35 | non-brittle; non-tacky |
| 2 | 6.15 | non-brittle; non-tacky |
| 3 | 6.2 | non-brittle; non-tacky |
| 4 | 6.58 | non-brittle; non-tacky |
| 5 | 14.0 | tacky |
| 6 | 1.0 | brittle |

The foregoing description and Examples illustrate select embodiments of the present invention. In light thereof, various modifications would be suggested to one skilled in the art all of which are within the purview and spirit of this invention.

What is claimed is:

1. A cosmetic product for removing keratotic plugs from skin pores comprising:
   (A) a strip comprising:
      (i) a flexible substrate sheet; and
      (ii) a composition containing a polymer selected from the group consisting of anionic, cationic, nonionic, amphoteric, zwitterionic and polymer mixtures thereof deposited onto the substrate sheet, the composition being dry non-tacky to the touch after deposition and upon being wetted for use the composition turns tacky and mobile; and
   (B) a foil pouch sealably enclosing the strip, a volatile fluid being selected from the group consisting of water, alcohol and mixtures thereof also being enclosed present in an amount from 2 to 12% by weight of the strip so that the strip does not stick to walls of the pouch.

2. The product according to claim 1 wherein the fluid is water and is present in an amount from 3 to 10% by weight of the strip.

3. The product according to claim 2 wherein the water is present in an amount from 4 to 8% by weight of the strip.

4. The product according to claim 1 wherein the substrate is a breathable fabric.

5. The product according to claim 4 wherein the fabric is rayon.

6. The product according to claim 1 wherein the composition and substrate are present in a weight ratio ranging from 0.1:1 to 1,000:1.

7. The product according to claim 1 wherein the amount of polymer ranges from 50 to 100% by weight of composition deposited onto the substrate sheet.

8. The product according to claim 1 wherein the polymer is a polyvinyl pyrrolidone.

9. The product according to claim 1 wherein the polymer is water-soluble.

10. The product according to claim 1 wherein the polymer is a poly(methyl vinyl ether/maleic anhydride) copolymer.

11. The product according to claim 1 wherein mobility of the composition is characterized by a yield point ranging from 1 to 400 Pascals.

12. A method for removing keratotic plugs from skin pores comprising:
   (a) providing a keratotic plug removing product as a strip enclosed within a sealed foil pouch, the pouch also enclosing a volatile fluid present in an amount from 2 to 12% by weight of the strip so that the strip does not stick to walls of the pouch, the volatile fluid being selected from the group consisting of water, alcohol and mixtures thereof, the strip comprising:
      (i) a flexible substrate sheet; and
      (ii) a composition containing a polymer selected from the group consisting of anionic, cationic, nonionic, amphoteric, zwitterionic and polymer mixtures thereof deposited onto the substrate sheet, the composition being dry non-tacky to the touch after deposition and upon being wetted for use the composition turns tacky and mobile;
   (b) removing the strip from the sealed pouch;
   (c) wetting an area of skin to be treated with a wetting agent;
   (d) applying the strip onto the area;
   (e) allowing the wetting agent to tackify the composition and then to evaporate from the area covered by the strip; and
   (f) peeling away the strip from the skin thereby removing keratotic plugs now adhesively attached to the composition.

13. A method for removing keratotic plugs from skin pores through use of a cosmetic product, the product comprising:

(1) a strip comprising:
   (i) a flexible substrate sheet;
   (ii) a composition containing a polymer selected from the group consisting of anionic, cationic, nonionic, amphoteric, zwitterionic and polymer mixtures thereof deposited onto the substrate sheet, the composition being dry non-tacky to the touch after deposition and upon being wetted for use the composition turns tacky and mobile; and (2) a foil pouch sealably enclosing the strip, a volatile fluid also being enclosed present in an amount from 2 to 12% by weight of the strip so that the strip does not stick to walls of the pouch, the volatile fluid being selected from the group consisting of water, alcohol and mixtures thereof; the method comprising:

(a) removing the strip from the pouch;
(b) wetting a surface of the strip with a wetting agent thereby turning the composition into a tacky and mobile material;
(c) applying the wetted strip onto an area of skin to be treated;
(d) allowing the wetting agent to evaporate from the area covered by the strip; and
(e) peeling away the strip from the skin thereby removing keratotic plugs now adhesively attached to the composition.

* * * * *

UNITED STATES PATENT AND TRADEMARK OFFICE
CERTIFICATE OF CORRECTION

PATENT NO. : 5,993,838
DATED : November 30, 1999
INVENTOR(S) : Crotty et al.

It is certified that error appears in the above-indentified patent and that said Letters Patent is hereby corrected as shown below:

In the Inventors' Section please change "Johnson Anthony"

to -- Anthony Johnson -- .

Signed and Sealed this

Twenty-fifth Day of July, 2000

Attest:

Q. TODD DICKINSON

Attesting Officer

Director of Patents and Trademarks